United States Patent [19]

Ng

[11] Patent Number: 4,947,841
[45] Date of Patent: Aug. 14, 1990

[54] NEONATAL MUCUS EXTRACTOR

[76] Inventor: Raymond C. Ng, 5238 Dona Maria La., La Canada, Calif. 91011

[21] Appl. No.: 273,022

[22] Filed: Nov. 18, 1988

[51] Int. Cl.[5] ............................................ A61M 16/00
[52] U.S. Cl. ............................... 128/207.14; 128/760; 604/319
[58] Field of Search ........................ 128/207.14, 207.15, 128/200.26, 10, 760; 604/19, 27, 35, 76, 319; 215/1 C, DIG. 3

[56] References Cited

U.S. PATENT DOCUMENTS

| | | | |
|---|---|---|---|
| Re. 29,321 | 7/1977 | Holbrook | 604/319 |
| 1,137,388 | 4/1915 | Earp-Thomas | 215/DIG. 3 |
| 2,700,973 | 2/1955 | Ju | 604/76 |
| 3,610,242 | 10/1971 | Sheridan . | |
| 4,207,894 | 6/1980 | Klibansky | 604/319 |
| 4,317,525 | 3/1982 | Schuessler et al. | 215/1 C |
| 4,321,921 | 3/1982 | Laszczower | 604/35 |
| 4,460,361 | 7/1984 | Nichols | 604/319 |
| 4,662,367 | 5/1987 | Gore, Jr. | 128/202.28 |
| 4,787,894 | 11/1988 | Turnbull | 604/319 |
| 4,791,914 | 12/1988 | May | 128/10 |
| 4,799,925 | 1/1989 | Rosenblatt | 215/DIG. 3 |
| 4,813,931 | 3/1989 | Hauze | 128/760 |

Primary Examiner—Edgar S. Burr
Assistant Examiner—Aaron J. Lewis
Attorney, Agent, or Firm—William W. Haefliger

[57] ABSTRACT

A suctioning device is provided for use in removal of fluid mucous from the trachea and nostrils of a newborn infant, to prevent aspiration of such fluid into the infant's lungs before first breath; the device includes:

(a) a vertically, longitudinally upright container having a bottom wall with an opening therein to pass mucous into the container via a tubular catheter, and a top cap with an opening therein to pass suction air from the container interior toward a suction mouthpiece,
(b) a baffle or baffles means in the container to intercept upward flow of mucous toward the top cap,
(c) a duct in the container to receive flow of mucous via the opening in the bottom wall, the duct having an outlet end located to eject mucous in a generally downward direction in the container, below the baffle.
(d) and a filter above the baffle, to filter air being sucked from the container interior toward the mouthpiece via the top cap opening.

9 Claims, 1 Drawing Sheet

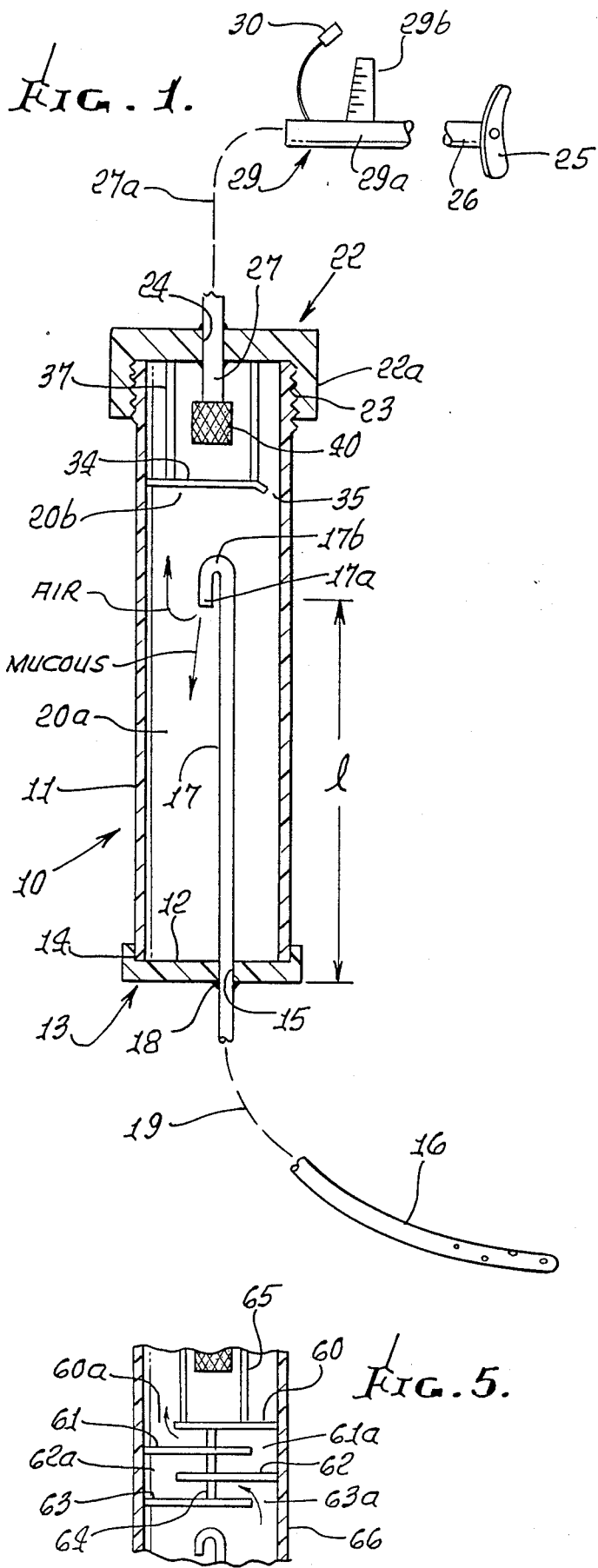
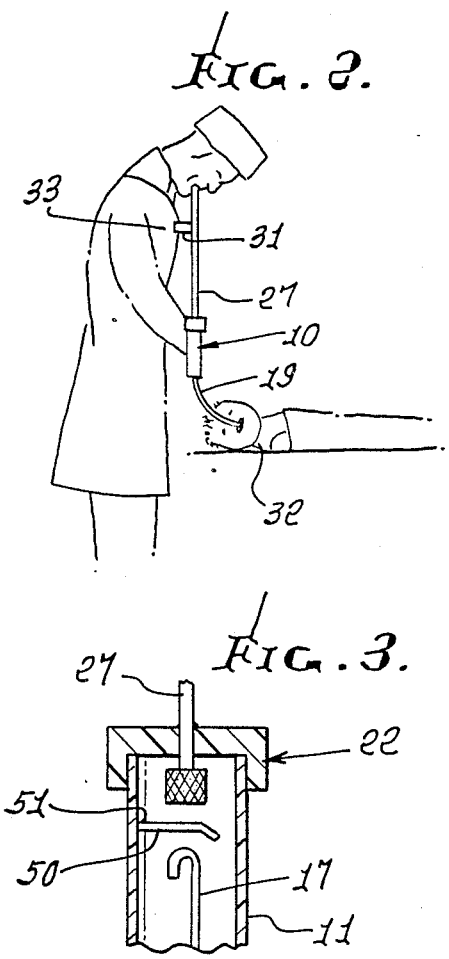
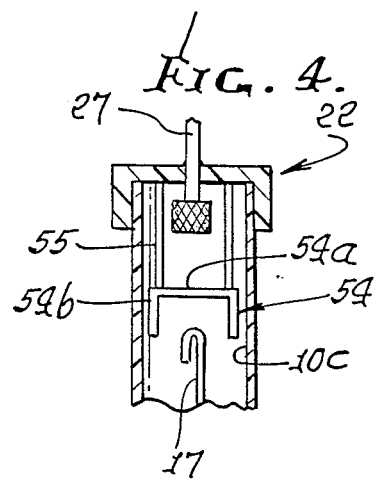

NEONATAL MUCUS EXTRACTOR

BACKGROUND OF THE INVENTION

The invention relates generally to a simple oral and mechanical suctioning of mucus and debris from a newborn infant's mouth and nostrils at the time of birth to prevent aspiration of such fluids into the lungs before the first breath.

Suctioning devices currently in use consist of a container with both an oral catheter (to the infant's mouth) and the suction tubing (to the operator for oral suctioning) attached to one end of the container in close proximity to each other, often resulting in the incidental contact on the operator of fluids and debris from the infant Such fluids sometimes can contain infectious agents (i.e. Hepatitis, AIDS virus, etc.).

There is great need for improved suctioning means that eliminates the above problem, and which also makes the suctioning device easier to employ, and to support during use.

SUMMARY OF THE INVENTION

It is a major object of the invention to provide an improved device that allows efficient suctioning of the newborn infant's mouth and nostrils at the time of birth, and at the same time eliminates the possibility of suctioning such fluids into the operator's mouth, for safety reasons.

This is made possible in accordance with the invention by separating the suction tubing and the oral catheter to connect to the two opposite ends of the mucous container and also by interrupting the air flow through the container during suctioning by incorporating a deflecting baffle means. The air flow is typically further diverted away from the suctioning tubing by a tube with a bent open end inside the container, and connected to the oral catheter.

Also, the invention allows a more efficient way to suction the infant's mouth as a full view of the infant's oral cavity is possible without blockage by the device itself This objective is realized by provision for support of the device, as will appear.

Basically, the invention is embodied in a device that comprises:

(a) a vertically, longitudinally, upright container including bottom and top walls, a lower opening into the container to pass mucous into the container via a tubular catheter, and an upper opening in the container to pass suction air from the container interior toward a suctioning mouthpiece, (b) first and second means within the container and at lengthwise spaced elevations therein, for preventing aspiration of mucous from the tube interior to pass upwardly via said top opening, (c) and flexible means supporting the container to hang vertically.

As will appear, third means separating air and mucous may also be provided in the container, and the first, second and third means may typically include, respectively, in sequence, a duct to direct flow of fluid downwardly in the container, a baffle extending sidewardly in the container to intercept upward flow of mucous, and a filter above the baffle.

Further objects includes the provision of a duct that extends generally vertically in the container toward the baffle means, and has a downward bent outlet end portion; the provision of baffle means that extend generally laterally in the container, to form with the side wall an air passing opening or openings adjacent said side wall; the provision of baffle means supported by a removable top cap, whereby the baffle means and filter may both be removed as a unit, with the top cap, from the container; the provision of various unusually advantageous baffle configurations, as will appear; and provision for full viewing of the container and bent duct contents.

These and other objects and advantages of the invention, as well as the details of an illustrative embodiment, will be more fully understood from the following specification and drawings, in which:

DRAWING DESCRIPTION

FIG. 1 is a vertical elevation in section showing one form of the device of the invention;

FIG. 2 is a view showing suspension of the device from the user's clothing, during use of the device;

FIGS. 3, 4, and 5 are fragmentary sections showing modified baffle arrangements.

DETAILED DESCRIPTION

In FIG. 1, a tubular container 10 is longitudinally, vertically oriented. It has a transparent side wall 11 via which the extent of mucous filling into the container can be viewed. The container may consist for example of synthetic resin, i.e. plastic material.

The container has a bottom wall 12, as may be formed by a bottom cap 13 attached to the lowermost extent of the container, as at 14. A suitable adhesive may provide the attachment. The bottom wall has an opening 15 therein, to pass mucous into the container as from a tubular catheter 16. The latter is typically inserted into the infant's trachea, at birth, to remove mucous prior to first breath.

A duct 17 extends upright within the container to receive flow of air entrained mucous entering the container via opening 15, and for this purpose, the duct may pass through the opening and be attached to the bottom wall, as by adhesive at 18. The duct connects with the catheter via a flexible duct 19. The duct 17 within the container is substantially rigid to stand upright. The duct may typically have an outlet opening 17a directed downwardly, and for this purpose the uppermost extent 17b of the duct may be bent or curved reversely, to open at 17a, generally downwardly. Entering air then separates from entrained mucous in the lower interior of the container. Thus, mucous leaving the tract during suction into the container is directed toward the lower interior 20a of the container, i.e. away from the upper interior 20b to which suction is applied. Note that bent portion 17b is well above the bottom wall 12 to provide mucous fill space of a length "l", which is typically more than half the overall length of the tubular container. Outlet 17a should remain above the mucous filling the container, the level of which may be viewed via the transparent wall of the container. Duct 17 typically consists of transparent plastic, i.e. has a transparent side wall.

A top cap 22 is provided to close the uppermost extent of the container. It advantageously has a skirt 22a removably thread connected to the container at 23, whereby the cap may be quickly removed, if necessary, as for pour-out removal of mucous from the container. The two caps 13 and 22 may also consist of plastic material.

The top cap has an opening 24 therein to pass suction air from the container interior, as toward a mouthpiece 25 connected in series with flexible tubing 26. A flexible duct 27 is typically connected with the mouthpiece and extends freely at 27a to support the container to hang vertically Duct 27 also may extend into the container upper interior via opening 24, and the duct may be attached to the top cap as by suitable adhesive, or other means. An aspiration control 29 may be connected in series with the duct 27 whereby variable aspiration control is obtained. Note that 29 includes a tubular main leg 29a in series with duct 27, and a tubular side leg 29b branching from 29a. A plug 30 may be fitted into the end of leg 29b to close it; otherwise, variable finger closure of the open end of leg 29b allows variable control of aspiration FIG. 2 shows a clip 31 on the duct 27 to attach to the user's clothing 33, and thereby suspend the device to hang freely vertically, during aspiration of the infant, seen at 32.

The baffle means is provided in the container to intercept upward flow of mucous in the air being removed by suction from the container interior via duct or tube 27. The baffle 34 extends laterally in FIG. 1 to block the direct upward flow of mucous while passing suction air. See narrow gap 35 at the edge of the baffle, and located between the edge and a small extent (less than 60° about the tube axis) of the container inner wall. The baffle is suspended by hanger 37 from the top cap 22. A mucous filter 40 is located above the baffle, at the lower end of duct 27, to remove any remaining mucous from the leaving air stream. Thus, when the top cap is removed, mucous may be poured from the container, the baffle and filter being attached to the top cap. This also facilitates direct inspection of the baffle and filter In FIG. 3, the baffle 50 is like 34, but it is attached to the container wall at 51, about that wall circumference, except for the gap area.

In FIG. 4, the baffle 54 has a top lateral wall 54a suspended at 55 from the top cap 22 so that the periphery of wall 54a is narrowly spaced from the container inner wall 10c. Also, it has an annular skirt 54b that depends to form a narrow gap 56 with wall 10c. That gap passes suction air upwardly, while the baffle top wall 54a blocks upward flow of mucous.

In FIG. 5, a vertical succession of lateral baffles or plates 60-63 is connected together at 64, and the top baffle suspended at 65 from the top cap, as before. Staggered air passing gaps are provided by baffle edges with the container wall 66, as at 60a-63a. This provides a tortuous air path which effectively blocks upward flow of mucous to the filter.

I claim:

1. In a suctioning device for use in removal of fluid mucous from the trachea and nostrils of a newborn infant, to prevent aspiration of such fluid into the infant's lungs before first breath, the combination comprising:
    (a) a vertically, longitudinally upright container having a bottom wall with an opening therein to pass mucous into the container via a tubular catheter, and a top cap including permanently attached hanger means extending into said container and with an opening therein to pass suction air from the container interior toward a suction mouthpiece,
    (b) baffle means in the container to intercept upward flow of mucous toward the top cap, the baffle means extending generally laterally in the container,
    (c) a duct in the container to receive flow of mucous via said opening in the bottom wall, the duct having an outlet end located to eject mucous in a generally downward direction in the container,
    (d) and a filter above the baffle, to filter air being sucked from the container interior toward the mouthpiece via the top cap opening, the filter located proximate the top cap and in alignment with the suction tubing,
    (e) said hanger means suspended the baffle means and filter from the top cap to be located above said duct, said top cap being removable to allow quick access to said baffle means and filter, and pour out of mucous.

2. The combination of claim 1 wherein the duct extends generally vertically in the container toward the baffle means, and has a downwardly bent outlet end portion.

3. The combination of claim 1 wherein the container has a transparent upright wall for viewing of the duct and baffle means.

4. The combination of claim 3 wherein the baffle means extends generally laterally in the container to form with said upright wall in air passing opening or openings closely adjacent said upright wall.

5. The combination of claim 3 wherein the duct has a transparent side wall.

6. The combination of claim 1 including flexible suction tubing attached to the top cap, and suspending the container to hang vertically.

7. The combination of claim 1 wherein the baffle means includes a series of baffles forming with the container a tortuous air flow path.

8. The combination of claim 1 wherein the baffle means includes a lateral wall and an annular skirt spaced narrowly from an inner wall defined by the container.

9. The device of claim 6 including means on the suction tubing to suspend the device from a user, to hang freely with the container oriented vertically during use of device to aspirate mucous from the infant.

* * * * *